(12) United States Patent
Bär et al.

(10) Patent No.: US 9,730,899 B2
(45) Date of Patent: Aug. 15, 2017

(54) CONTROLLED RELEASE PHARMACEUTICAL COMPOSITION WITH RESISTANCE AGAINST THE INFLUENCE OF ETHANOL EMPLOYING A COATING COMPRISING NEUTRAL VINYL POLYMERS AND EXCIPIENTS

(75) Inventors: Hans Bär, Brombachtal (DE); Thomas Fürst, Frankfurt (DE); Gerhard Renner, Stockstadt am Rhein (DE); Michael Gottschalk, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 1055 days.

(21) Appl. No.: 13/256,694

(22) PCT Filed: Mar. 18, 2009

(86) PCT No.: PCT/EP2009/053176
§ 371 (c)(1),
(2), (4) Date: Sep. 15, 2011

(87) PCT Pub. No.: WO2010/105672
PCT Pub. Date: Sep. 23, 2010

(65) Prior Publication Data
US 2012/0045506 A1    Feb. 23, 2012

(51) Int. Cl.
*A61K 9/52* (2006.01)
*A61K 9/14* (2006.01)
*A61K 31/485* (2006.01)
*A61K 9/50* (2006.01)

(52) U.S. Cl.
CPC .................................. *A61K 9/5078* (2013.01)

(58) Field of Classification Search
None
See application file for complete search history.

(56) References Cited

U.S. PATENT DOCUMENTS

| | | | |
|---|---|---|---|
| 2004/0202717 A1* | 10/2004 | Mehta | 424/471 |
| 2005/0079216 A1* | 4/2005 | Petereit et al. | 424/464 |
| 2005/0163856 A1 | 7/2005 | Maloney et al. | |
| 2006/0204576 A1 | 9/2006 | Petereit et al. | |
| 2008/0020032 A1 | 1/2008 | Crowley et al. | |
| 2008/0069871 A1 | 3/2008 | Vaughn et al. | |
| 2008/0075768 A1 | 3/2008 | Vaughn et al. | |
| 2008/0075770 A1 | 3/2008 | Vaughn et al. | |
| 2008/0075771 A1 | 3/2008 | Vaughn et al. | |
| 2008/0193522 A1 | 8/2008 | Meier et al. | |
| 2010/0221324 A1 | 9/2010 | Petereit et al. | |
| 2010/0226978 A1 | 9/2010 | Petereit et al. | |
| 2011/0217383 A1 | 9/2011 | Baer et al. | |
| 2011/0229562 A1 | 9/2011 | Baer et al. | |

FOREIGN PATENT DOCUMENTS

| | | | |
|---|---|---|---|
| IN | WO 2009036812 | * | 3/2009 |
| JP | 2006-501261 | | 1/2006 |
| WO | 2004/022038 A1 | | 3/2004 |
| WO | 2004 039357 | | 5/2004 |
| WO | 2006 125483 | | 11/2006 |
| WO | 2007 053698 | | 5/2007 |
| WO | 2007 085024 | | 7/2007 |
| WO | 2008 011595 | | 1/2008 |
| WO | 2008 049657 | | 5/2008 |

OTHER PUBLICATIONS

International Search Report Issued Jul. 6, 2009 in PCT/EP09/053176 Filed Mar. 18, 2009.
U.S. Appl. No. 13/203,760, filed Aug. 29, 2011, Baer, et al.
Notification of Reasons for Refusal issued Jul. 29, 2013, in Japanese Patent Application No. 2012-500078 filed Mar. 18, 2009.

* cited by examiner

*Primary Examiner* — Tigabu Kassa
(74) *Attorney, Agent, or Firm* — Oblon, McClelland, Maier & Neustadt, L.L.P.

(57) ABSTRACT

The invention relates to a controlled release pharmaceutical composition, comprising a core, comprising a pharmaceutical active ingredient, whereby the core is coated by an ethanol resistance conferring coating layer which has the effect of conferring the release profile of the pharmaceutical active ingredient to be resistant against the influence of ethanol, whereby the ethanol resistance conferring coating layer comprises at least 70% by weight of a mixture of a polymeric portion a) and an excipients portion b), with the polymeric portion a) is consisting of a water insoluble essentially neutral vinyl polymer or vinyl copolymer and the excipients portion b) is consisting of the excipients b1) 100 to 250% by weight of a non-porous inert lubricant, b2) 1 to 35% by weight of a cellulosic compound, b3) 0.1 to 25% by weight of an emulsifier and additionally or alternatively to b3), b4) 0.1 to 30% by weight of a plasticizer whereby the excipients of the excipients portion b) are each calculated on the dry weight of the polymer portion a).

36 Claims, No Drawings

CONTROLLED RELEASE PHARMACEUTICAL COMPOSITION WITH RESISTANCE AGAINST THE INFLUENCE OF ETHANOL EMPLOYING A COATING COMPRISING NEUTRAL VINYL POLYMERS AND EXCIPIENTS

FIELD OF INVENTION

The invention relates to the field controlled release pharmaceutical compositions with resistance against the influence of ethanol.

TECHNICAL BACKGROUND

US 2003/0118641 A1 describes a procedure for reducing the abuse potential of oral pharmaceutical forms which contain extractable opioids. In this procedure, resistance to active compound extraction by means of customary domestic solvents, such as isopropyl alcohol, vodka, white wine vinegar, hot water or peroxides, 0.01 HCl in diluted alcohol, should in particular be brought about. It is proposed to formulate the active compound with a matrix-forming polymer and an ion exchange material, e.g. styrene-divinylbenzene polymers, in micronized form. The ion exchange material is crucial for the function of increased resistance to active compound extraction. The matrix-forming polymer obviously serves as a structure-imparting agent for the pharmaceutical core. A long list of possible substances is specified for the matrix-forming polymers, which among many other substances also comprises polymethacrylates. Preferred matrix-forming agents are $C_1$-$C_6$-hydroxyalkylcelluloses.

US 2004/0052731 A1 describes a pharmaceutical form, in particular suitable for opioid active compounds, which should contribute to the reduction of the abuse potential as a result of improper administration. It is proposed to combine a lipophilic active compound variant with a water-insoluble additive, such as, for example, a fatty acid or crosslinked water-soluble polysaccharides.

US 2005/0163856 A1 describes a therapeutic procedure for the treatment of patients suffering from pain with an oxycodone-containing pharmaceutical form having reduced abuse potential as a result of dissolution in a solvent and subsequent improper administration. To this end, the active compound should be formulated with a matrix-forming polymer selected from the group consisting of hydroxypropyl-cellulose, hydroxypropylmethylcellulose or hydroxyethylcellulose.

WO 2006/094083 A1 describes a pharmaceutical form having controlled venlafaxine release characteristics. For the reduction of the abuse potential by addition of ethanol, the active compound is integrated into a matrix of a gelling, crosslinked polymer, e.g. xanthan. Further hydrophobic polymers, inter alia also polymethacrylates, can be added as additives.

WO 1994/022431 A1 describes an oral pharmaceutical preparation containing a therapeutically effective amount of morphine for administration. It consists of at least 50 individual particles with an individual particle size in the range of 0.7 to 1.4 mm. Each particle has a core containing a salt of morphine coated with a barrier layer. The barrier layer contains at least one water insoluble component selected from the group of ethyl cellulose, copolymers synthesized from acrylic or methacrylic esters and natural waxes, and a plasticizer, for providing drug release through the coating barrier layer which is substantially independent of pH in the range of 1.0 to 7.0. The resulting serum concentration of morphine obtained is at least 50% of the maximum serum concentration during at least 12 hours after the administration of a single dose of said preparation.

US 2007/053698 discloses methods of sustained release administration of opioids, including but not limited to hydromorphone and oxycodone, that exhibit improved properties with respect to co-ingestion with aqueous alcohol.

Problem and Solution

Pharmaceutical compositions are designed to release the active ingredient in a manner of reproducible release profiles. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non-optimal blood level concentrations of an active ingredient can be dangerous for the patient and shall therefore be avoided. A problem exists in that the ideal ratios assumed for the release of active ingredient during the design of a pharmaceutical composition can be altered by the general living habits, thoughtlessness or by addictive behaviour of the patients with respect to the use of ethanol or ethanol-containing drinks. In these cases, the pharmaceutical form which is actually designed for an exclusively aqueous medium is additionally exposed to an ethanol containing medium of greater or lesser strength. Since health authorities like for instance the Food and Drug Administration (FDA) focus more and more on the ethanol problem, ethanol resistance may be an important registration requirement in the near future.

Since not all patients are aware of the risk of simultaneous taking of a controlled release pharmaceutical form and ethanol-containing drinks or do not follow or are not able to follow appropriate warnings, advice or recommendations, the object is to design controlled release pharmaceutical compositions such that their mode of action is affected as little as possible by the presence of ethanol.

Conventional pharmaceutical compositions if coated or uncoated are usually not resistant to alcohol at all. The problem of the present invention was to provide controlled release pharmaceutical compositions which are resistant against the influence of ethanol. The means taken should be versatile and applicable to existing controlled release pharmaceutical compositions without essentially altering their already optimized release profiles. The means taken should also be versatile and applicable for the design of new controlled release pharmaceutical compositions and adaptable for a wide range of pharmaceutical active ingredients.

The problems and objects are solved by a controlled release pharmaceutical composition, comprising:

a core, comprising a (one or more) pharmaceutical active ingredient, whereby the core is coated by an ethanol resistance conferring coating layer which has the effect of conferring the release profile of the pharmaceutical active ingredient to be resistant against the influence of ethanol under in-vitro conditions at pH 1.2 and/or at pH 6.8 in a buffered medium according to USP with the addition of 40% (v/v) ethanol, whereby resistant against the influence of ethanol means that the release profile is not accelerated by more than 20% and not delayed by more than 20% under the influence of the 40% ethanol containing medium in comparison to a release profile determined in the same medium without ethanol, whereby the ethanol resistance conferring coating layer
comprises at least 70% by weight of a mixture of a
polymeric portion a) and an excipients portion b)
whereby
the polymeric portion a) is consisting of
  a water insoluble, essentially neutral vinyl polymer or
    vinyl copolymer
and the excipients portion b) is consisting of the excipients
  b1) 100 to 250% by weight of a non-porous inert
    lubricant,
  b2) 1 to 35% by weight of a cellulosic compound,
  b3) 0.1 to 25% by weight of an emulsifier and additionally or alternatively to b3),
  b4) 0.1 to 30% by weight of a plasticizer
whereby the excipients of the excipients portion b) are
  each calculated on the dry weight of the polymer
  portion a).

Starting from a given core with a certain active ingredient and a desired release profile, a skilled person can use the elements of the polymeric portion a) and the excipients portion b) to adjust a balance between acceleration and delay in the media with ethanol to match the desired release profile in media with and without ethanol as close as possible. As a further adjustment tool the skilled person may also employ the thickness of the ethanol resistance conferring coating layer.

Pharmaceutical Composition

The term pharmaceutical composition according of the present invention shall be understood in a broad way. The term includes such pharmaceutical compositions which require high standards for approval by the health authorities as well as such pharmaceutical compositions which have lower approval requirements or do not need to have special approvals at all, for instance so called medical devices or nutraceuticals.

A Controlled Release Pharmaceutical Composition

A controlled release pharmaceutical composition means a pharmaceutical composition including an active pharmaceutical ingredient which is formulated with pharmaceutically acceptable film forming polymers and optionally with pharmaceutically acceptable excipients, where the pharmaceutical composition shows a pH-dependent or a pH-independent reproducible release profile. Examples for controlled release pharmaceutical compositions are immediate release pharmaceutical compositions, enteric coated pharmaceutical compositions, pulsed release pharmaceutical compositions or sustained release pharmaceutical compositions.

Pharmaceutical Active Ingredients
Classification of the Solubility in Water or in Ethanol The present invention refers to the Classification of the solubility of pharmaceutical active ingredients in water or in ethanol according to the USP Pharmacopeia reference tables, which are cited here:

| Classification | Parts of solvent required for one part of solute (between 15° C. and 25° C.) |
| --- | --- |
| Very soluble | less than 1 |
| Freely soluble | from 1 to 10 |
| Soluble | more than 10 to 30 |
| Sparingly soluble | more than 30 to 100 |
| Slightly soluble | more than 100 to 1000 |
| Very slightly soluble | more than 1000 to 10.000 |
| Practically insoluble | more than 10.000 |

Examples:

| Drug | Solubility in water | Solubility in ethanol |
| --- | --- | --- |
| Morphine sulfate | Soluble | Slightly soluble |
| Diltiazem HCl | Freely soluble | Sparingly soluble |
| Metoprolol succinate | Freely soluble | Sparingly soluble |
| Carbamazepine | Practically insoluble | Soluble |
| Theophylline | Slightly soluble | Sparingly soluble |
| Naloxone | Soluble | Slightly soluble |
| Mesalazine | Very slightly soluble | Practically insoluble |

The Controlled release pharmaceutical composition according to the present invention may be used for pharmaceutical active ingredients which have a solubility in ethanol which is classified as slightly soluble, such as opioids, for instance morphine sulfate, or opioid antagonists, for instance naloxone. The solubility in water is preferably classified as soluble.

The Controlled release pharmaceutical composition according to the present invention may be used for pharmaceutical active ingredients which have a solubility in ethanol which is classified as sparingly soluble, such as diltiazem, metoprolol or theophyllin. The solubility in water in this case may range from freely soluble to slightly soluble.

The Controlled release pharmaceutical composition according to the present invention may be used for pharmaceutical active ingredients which have a solubility in ethanol which is classified as practically insoluble, such as Mesalazine. The solubility in water in this case is very slightly soluble but may range from soluble to very slightly soluble.

Active Substances

The multilayer dosage form according to the invention is theoretically suitable for any active substance. Information about conventional medicinal products can be found in reference books such as the German Red List or the Merck Index.

The drugs utilized within the scope of the invention are intended for use on or in human or animal bodies to
  1. heal, relieve, prevent or detect illness, disease, bodily injury or pathological complaints;
  2. identify the condition, state or functioning of the body, or mental states;
  3. replace active substances or bodily fluids produced by the human or animal body;
  4. ward off, eliminate or neutralize pathogens, parasites or exogenous substances; or
  5. influence the condition, state or functioning of the body, or mental states.

The formulation according to the invention is suitable, in principle, for administering any active pharmaceutical substances or biologically active substances that preferably can be administered as an ingredient of a multiparticle dosage form, from tablets containing pellets, minitablets, capsules, sachets, effervescent tablets or dry powders for oral suspension.

Therapeutic Classes

These pharmaceutically active substances can belong to one or more active substance classes, such as weight-reduction agents (appetite suppressants, anti-obesity agents), anti-acidosis agents, analeptics (antihypoxemics), analgesics (antirheumatics), anthelmintics, antiallergics, antianemics, anti-arrhythmic agents, antibiotics (anti-infectives), anti-dementia agents (nootropics), anti-diabetics, antidotes, antiemetics (antivertiginous agents), anitepileptics, antihemorrhagic agents (antifibrinolytics and other hemostatics), antihypertensives, antihypoglycemic agents, antihypotensive agents, anticoagulants, antimycotics, antiparasitic agents, antiphlogistics, antitussives (expectorants), anti-arteriosclerosis agents, balneotherapeutic agents and agents for heat therapy, beta-receptor blockers, calcium channel blockers and renin-angiotensin-aldosterone system inhibitors, bronchiolytics (antiasthmatics), cholagogues and biliary tract therapeutics, cholinergics, corticoids, dermatic agents, disinfectants (antiseptics), dietetic agents (nutritional agents), diagnostic agents and agents for preparing diagnoses, diuretics, agents that promote blood circulation, withdrawal agents (agents for treating addiction), enzyme inhibitors, preparations for enzyme deficiency, transport proteins, fibrinolytics, geriatrics, antigout preparations, cold and flu remedies and remedies for coughs and sneezing, gynecological remedies, hemorrhoid remedies (proctologics), hepatics, hypnotics (sedatives), hypophysis hormones, hypothalamus hormones and other regulatory peptides and their inhibitors, immune modulators, infusion and standard injection solutions, organ perfusion solutions, cardiac agents, anti-caries agents, periodontosis remedies and other dental preparations, coronary preparations, laxatives, lipid-lowering agents, local anesthetics (neural therapeutics), gastrointestinal remedies, migraine remedies, mineral preparations, oral and pharyngeal remedies, muscle relaxants, anesthetics, neuropathy preparations and other neurotropic agents, ophthalmics, anti-osteoporosis agents (calcium- and bone metabolism regulators), otologic agents, anti-Parkinson's agents and other remedies for extrapyramidal disorders, psychopharmaceuticals, rhinologics (sinus remedies), roborantia (tonics), thyroid preparations, sera, immunglobulins and vaccines, sexual hormones and their inhibitors, spasmolytics (anticholinergics), thrombocyte aggregation inhibitors, tuberculosis remedies, Umstimmungsmittel, urologics, remedies for venous disorders, vitamins, wound and scar treatment agents, cytostatiks and other antineoplastisic agents and protectives, biomaterials, medical synthetics.

Active Substances

Examples of suitable active substances include 5-amino salicylic acid, abacavir, abarelix, abatacept, acamprosate, acarbose, aceclofenac, acetylsalicylic acid, acitretin, aclarubicin, actinomycin, acyclovir, adalimumab, adefovir, adefovir dipivoxil, adenosine, adenosyl methionine, adrenaline, adriacin, agalsidase alpha, agalsidase beta, aldesleukin, alefacept, alemtuzumab, alendronate, alfacalcidol, alfuzosin, alglucosidase alfa, aliskiren, alitretinoin, allopurinol, almotriptan, alosetron, alefacept, alprazolam, alprostadil, amantadine, ambrisentan, ambroxol, amifostin, amiodarone, amisulpride, amitriptyline, amlodipine, amoxicillin, amphotericin B, amprenavir, anagrelide, anakinra, anastrozole, androgen, thiamin (aneurin), anidulafungin, apomorphine, aprepitant, aprotinin, argatroban, aripiprazole, arsentrioxide, artemether, ascorbic acid, atazanavir, atenolol, atomoxetine, atorvastatin, atosiban, axerophthol, azathioprine, azelaic acid, azithromycin, aztreonam, balsalazide, barbituric acid derivates, basiliximab, beclapermin, beclometasone, bemiparin, benazepril, benidipine, benzodiazepine, betahistin, betamethasone, bevacizumab, bexarotene. bezafibrate, bicalutamide, bimatoprost, biotin, bisoprolol, bivalirudin, bortezomib, bosentan, botulinum toxin, brimonidine, brinzolamide, bucillamine, budesonide, budipine, bufexamac, bumetanide, buprenorphine, bupropion, butizine, calcitonin, calcium, calcium antagonists, candesartan, capecitabine, captopril, carbamazepine, carbetocin, carbidopa, carboplatin, carglumic acid, carvedilol, caspofungin, cefaclor, cefadroxil, cefalexin, cephalosporin, cefdinir, cefditoren, cefepime, cefixime, cefotiam, cefozopran, cefprozil, ceftriaxon, cefuroxime, celecoxib, cepecitabine, cerivastatin, cetirizine, cetrorelix, cetuximab, cevimeline, chenodeoxycholic acid, choriogonadotropin, ciclesonide, cyclosporine, cidofovir, cilastatin, cilostazol, cimetidine, cinacalcet, ciprofloxacin, cisplatin, citalopram, cladribine, clarithromycin, clavulanic acid, clindamycin, clobetasol, clobutinol, clofarabine, clonidine, clopidogrel, cobalamine, codeine, caffeine, colesevelam, cholestyramine, cotrimoxazole, cromoglicic acid, cromolyn, coumarin, cyclophosphamide, cyclosporine, cyproterone, cysteamine, cysteine, cytarabine, dabigatranetexilate, daclizumab, dalfopristine, danaparoid, dapiprazole, daptomycin, darbepoetin, darifenacin, darunavir, dasatinib, deferiprone, deferasirox, desipramine, desirudin, desloratadine, desmopressine, desogestrel, desonide, dexibuprofen, dexketoprofen, dexrazoxane, diazepam, dibotermin alfa, diclofenac, didanosine, dihydralazine, diltiazem, dimenhydrinate, dimethyl sulfoxide, dimethicone, dipivoxil, dipyridamole, disoproxil, disopyramide, divalproex, docetaxel, docosane-1-ol, dolasetron, domperidone, donepezil, dopamine, dornase alfa, dorzolamide, doxazosine, doxercalciferol, doxifluridine, doxorubicine, doxylamine, dronabinol, droperidol, drospirenone, drotrecogin alpha, duloxetine, dutasteride, ebastine, ecabet, econazole, eculizumab, efalizumab, efavirenz, eflornithine, eletriptan, emedastine, emtricitabine, enalapril, encepur, enfurvirtide, enoxaparin, entacapone, entecavir, epalrestat, ephedrine, epinastine, epinephrine, epirubicine, eplerenone, epoetin, eprosartan, eptacog alfa, eptifibatide, eptotermin alfa, erlotinib, ertapenem, escitalopram, esomeprazole, estradiol, estrogen, etanercept, ethenzamide, ethinyl estradiol, etofenamate, etofibrate, etofylline, etonogestrel, etoposide, etoricoxib, everolimus, exemestane, exenatide, ezetimibe, famciclovir, famotidine, farmorubicin, faropenem daloxate, felbinac, felodipine, fenofibrate, fentanyl, fenticonazole, fexofenadine, filgastrim, finasteride, fluconazole, fludarabine, flunarizine, fluorometholone, fluorouracil, fluoxetine, flupirtine, flurbiprofen, flutamide, fluticasone, fluvastatin, fluvoxamine, follitropin, folic acid, fomepizole, fomivirsen, fondaparinux, formoterol, fosamprenavir, fosaprepitant dimeglumine, fosfomicin, fosinopril, frovatriptan, fulvestrant, furosemide, fusidic acid, gabapentin, gadobenate, gadobenic acid, gadobutrol, gadodiamide, gadopentetic acid, galantamine, gallopamil, galsulfase, ganciclovir, ganirelix, gatifloxacin, gefitinib, gemcitabine, gemfibrozil, gentamicin, gepirone, gestagen, gestoden, ginkgo, glatiramer, glibenclamide, gliclazide, glimepiride, glipizide, glucagon, glucitol, glucosamine, glutathione, glyburide, glycerol, glycerol trinitrate, glycoside antibiotics, goserelin, granisetron, grepafloxacin, guanethidine, gyrase inhibitors, halofantrine, haloperidol, haemin, urea derivatives as oral antidiabetics, heparin, cardiac glycosides, hyaluronic acid, hydralazine, hydrochlorothiazide, hydroxy omeprazole, hydroxyzine, hypothalamus hormones, ibandronic acid, ibritumomab, ibuprofen, idarubicin, idursulfase, ifliximab, ifosfamide, iloprost, imatinib, imidapril, imiglucerase, imipenem, imipramine, imiquimod, indinavir, indometacin, indoramin, infliximab, insulin glargin, insulin, interferon, interleukin, iohexol, iopamidol, iopromide, iosarcol, ipratropium bromide, irbesartan, irinotecan, isoconazole, isoprenaline, isosorbide, itraconazole, ivabradine, iodine, St. John's wort, potassium salt, ketoconazole, ketoprofen, ketotifen, lacidipine, lamivudine, lamotrigine, lanreotide, lansoprazole, lanthanum carbonate, laronidase, latanoprost, leflunomide, lenalidomide, lepirudin, lercanidipine, leteprinim, letrozole, leuprolide, levacetylmethadol, levafloxacin, levetiracetam, levobupivacaine, levocabastin, levocetirizine, levodopa, levodropropizine, levofloxazine, levomethadone, levonorgestrel, levothyroxine, licofelone, lidocaine, limaprost, linezolid, liothyronine, liponic acid, lisinopril, lisuride, lodoxamide, lofepramine, lomefloxacin, lomustine, loperamide, lopinavir, loratadine, lornoxicam, losartan, loteprednol etabonate, lovastatin, loxoprofen, lumefantrine, lumiracoxib, lutropin, magnesium, macrolide antibiotics, mangafodipir, manidipine, maprotiline, maraviroc, maxacalcitol, mebendazole, mebeverine, mecasermin, meclozine, mefenamic acid, mefloquine, melatonin, meloxicam, melphalan, memantine, menaquinone, menadione, mepindolol, meprobamate, meropenem, mesalamine, mesalazine, mesuximide, metamizole, metaxalone, metformin, methadone, methotrexate, methoxy-polyethylene glycol-epoetin beta, methyl-(5-amino-4-opentanoate), methyl-(5-amino-4-oxopentanoate) methyl naloxone, methylnaltrexone, methylphenidate, methylprednisolone, metixen, metoclopramide, metoprolol, metronidazole, mianserin, mibefradil, micafungin, miconazole, mifepristone, miglitol, miglustat, minocycline, minoxidil, mirtazapine, misoprostol, mitomycin, mitoxantrone, mizolastine, modafinil, moexipril, mometasone furoate, montelukast, moroctocog alfa, morphine, mosapride, moxifloxacin, ergot alkaloids, mycophenolate mofetil, nadifloxacin, nadroparine calcium, naftidrofuryl, nalbuphine, naloxone, naproxen, naratriptan, narcotine, natalizumab, natamycin, nateglinide, sodium phenylbutyrate, nebivolol, nefazodone, nelarabine, nelfinavir, neostigmine, neramexane, nesiritide, nevirapine, niacin, nicardipine, nicergoline, nikethamide, nicorandil, nicotinic acid, nifedipine, niflumic acid, nilotinib, nilvadipine, nimodipine, nimorazole, nimustine, nisoldipine, nitisinone, norelgestromin, norfloxacin, noscapin, novaminsulfon, nystatin, octreotide, ofloxacin, octreotride, olanzapine, olmesartan, olopatadine, olsalazine, omalizumab, omeprazole, omoconazole, ondansetron, orlistat, oseltamivir, oxacephem, oxaceprol, oxacillin, oxaliplatin, oxaprozin, oxcarbazepine, oxiconazole, oxycodone, oxymetazoline, paclitaxel, palifermin, paliperidone, palivizumab, palonosetron, panipenem, panitumumab, pantoprazole, pantothenic acid, paracetamol, parathyroid hormone, parecoxib, paricalcitol, paroxetine, pegaptanib, pegaspargase, pegfilgrastrim, peginterferon, pemetrexed, penciclovir, penicillin (oral), pentazocine, pentifylline, pentoxifylline, peptide antibiotics, perflutren, perindopril, perphenazine, pethidine, plant extracts, phenazone, pheniramine, phenothiazines, phenserine, phenylbutazone, phenylbutyric acid, phenytoin, phylloquinone, pilsicainide, pimecrolimus, pimozide, pindolol, pioglitazone, piperacillin, piperazine, piracetam, pirenzepine, piribedil, pirlindole, piroxicam, porfimer, posaconazole, pramipexole, pramlintide, pranlukast, pravastatin, prazosin, pregabalin, procaine, promazine, propionic acid derivatives, propiverine, propofol, propranolol, propyphenazone, prostaglandins, protionamide, proxyphylline, pyridoxine, quetiapine, quinapril, quinupristin, rabeprazole, racecadotril, raloxifene, raltegravir, ramipril, ranibizumab, ranitidine, ranolazine, rasagiline, rasburicase, reboxetine, repaglinide, reproterol, reserpine, retapamulin, retinol, revofloxacin, ribavirin, riboflavin, rifampicin, rifaximin, riluzole, rimexolone, rimonabant, risedronate, risperidone, ritonavir, rituximab, rivastigmine, rizatriptan, rofecoxib, ropinirole, ropivacaine, rosiglitazone, rosuvastatin, rotigotine, roxatidine, roxithromycin, rufinamide, ruscogenin, rutoside, sabadilla, salbutamol, salicylic acid, salmeterol, saperconazole, sargramostim, thyroid hormones, scopolamine, selegiline, sertaconazole, sertindol, sertraline, sevelamer, sevofluran, sibutramine, sildenafil, silicate, simvastatin, sirolimus, sitagliptine, sitaxentan, sitosterol, sivelestat, solifenacin, somatropin, sorafenib, sotalol, spagluminic acid, sparfloxacin, spectinomycin, spiramycin, spirapril, spironolactone, stavudine, stiripentol, streptomycin, strontium ranelate, sucralfate, sufentanil, sulbactam, sulfasalazine, sulfonamide, sulpiride, sultamicillin, sultiame, sumatriptan, sunitinib, suxamethonium chloride, tacrine, tacrolimus, tadalafil, tafluprost, taliolol, talsaclidine, tamoxifen, tamsulosin, tandospirone, tasonermin, tazarotene, tazobactam, tegafur, tegaserod, telbivudine, telithromycin, telmisartan, temocapril, temoporfin, temozolomide, temsirolimus, tenatoprazole, tenecteplase, teniposide, tenofovir, tenoxicam, terazosin, terbinafine, terbutaline, terfenadine, teriparatide, terlipressin, tertatolol, testosterone, tetrabenazine, tetracycline, tetryzoline, tezosentan, theobromine, theophylline, thiamazole, thiamin, thiotepa, thrombin, thyrotropin alfa, thyroxine, tiagabine, tiapride, tibolone, ticlopidine, tigecycline, tilidine, timolol, tinidazole, tioconazole, tioguanine, tiotropium, thioxolone, tipranavir, tirofiban, tiropramide, tizanidine, tobramycin, tocopherol alpha/beta/gamma/delta, tolazoline, tolbutamide, tolcapone, tolnaftate, tolperisone, tolterodine, topiramate, topotecan, torasemide, trabectedin, tramadol, tramazoline, trandolapril, tranylcypromine, trapidil, trastuzumab, travoprost, trazodone, trepostinil, triamcinolone, triamterene, trifluperidol, trifluridine, trofosfamide, trimetazidine, trimethoprim, trimipramine, tripelennamine, triprolidine, tirofiban, tromantadine, trometamol, tropalpin, trovafloxacin, troxerutin, trypsin, tulobuterol, tyramine, tyrothricin, urapidil, ursodeoxycholic acid, ursodiol, valaciclovir, valdecoxib, valganciclovir, valproic acid, valsartan, vancomycin, vardenafil, vareniclin, vecuronium chloride, venlafaxine, verapamil, verteporfin, vidarabine, vigabatrin, vildagliptin, viloxazine, vinblastine, vincamin, vincristine, vindesine, vinorelbine, vinpocetine, viquidil, voglibose, voriconazole, warfarin, xantinol nicotinate, ximelagatran, xipamide, zafirlukast, zalcitabine, zaleplon, zanamivir, ziconotide, zidovudine, ziprasidon, zoledronic acid, zolmitriptan, zolpidem, zonisamide, zopiclone, zotepine and the like.

If desired, the active substances can also be used in the form of their pharmaceutically utilized salts or chemical derivatives with comparable or, if necessary, slightly altered spectrums of action, and in the case of chiral active substances, both optically active isomeres and racemic mixtures or diastereoisomeric mixtures can be used. If desired, the compounds of the invention can also contain two or more active pharmaceutical substances.

Ethanol Resistance Conferring Coating Layer

The term ethanol resistance conferring coating layer means a coating onto a core, comprising a pharmaceutical active ingredient, whereby the coating comprises at least 70, at least 80 at least 90, at least 95, at least 99 or 100% by weight of a mixture of a polymeric portion a) and an excipients portion b) whereby
  the polymeric portion a) is consisting of a water insoluble, essentially neutral vinyl polymer or vinyl copolymer and
  the excipients portion b) is consisting of the excipients
    b1) 100 to 250, 110 to 240, 150 to 220% by weight of a non-porous inert lubricant,
    b2) 1 to 35, 2 to 30, 5 to 28 or 15 to 25% by weight of a cellulosic compound,
    b3) 0.1 to 25, 0.8 to 20, 1 to 15 or 5 to 12% by weight of an emulsifier and additionally or alternatively to b3),
    b4) 0.1 to 30, 1 to 25, 2 to 22 or 5 to 15% by weight of a plasticizer
  whereby the excipients of the excipients portion b) are each calculated on the dry weight of the polymer portion a). The polymeric portion a) and the excipients portion b) are uniformly mixed with each other.

Resistance Against the Influence of Ethanol

Ethanol resistant pharmaceutical formulations are formulations with release kinetics not significantly affected in the presence of ethanol. Ethanol resistance may be an important registration requirement in the near future. Conventional pharmaceutical compositions if coated or uncoated are usually not resistant to alcohol at all. Surprisingly it was found that when coatings comprising an ethanol resistance conferring coating layer according to the present invention are applied to cores that are immediate release pharmaceutical compositions, sustained release pharmaceutical compositions, enteric coated pharmaceutical compositions or pulsed release pharmaceutical compositions these coatings provide an acceptable resistance against alcohol. An ethanol resistant formulation is sometimes also called a rugged formulation.

Resistance against the influence of ethanol (Ethanol resistant pharmaceutical formulations) is defined in that the release profile determined under in-vitro conditions at pH 1.2 and/or at pH 6.8 in a buffered medium according to USP with the addition of 40% (v/v) ethanol is not accelerated by more than 20%, preferably by not more than 10%, and not delayed by more than 20%, preferably by not more than 10%, under the influence of the 40% ethanol containing medium in comparison to a release profile determined in the same medium without ethanol. Generally an acceleration of a release profile is more critical than a delay. Therefore, the upper limit for an acceleration of the release profile is preferably not more than 10%, more preferably not more than 5%, even more preferably there is no acceleration of the release profile at all.

Depending on the certain pharmaceutical composition the applicable conditions of the USP test may vary for instance if the paddle or basket method has to be used or the stirring has to be 50, 100 or 150 rpm. For the determination of the ethanol resistance it does not matter which USP test is applied for the certain pharmaceutical composition as long as it is the relevant test for the certain pharmaceutical composition and the test conditions with and without ethanol are the same.

Resistance against the influence of ethanol in the sense of the present invention shall be tested in a relevant period of the release of the active ingredient, where meaningful results can be expected. The period which is meaningful chosen is from or between 10 to 80% of the total dosage release in the medium without ethanol. In this period the resistance against the influence of ethanol shall be determined at a number n of at least n=3, but preferably more than 3, for instance n=4, 5, 6, 7, 8, 9, 10, 11 or 12 uniformly distributed test points. The number of meaningful chosen test points depends on the total time period of the release profile from or between 10 to 80% of the total dosage release. The longer the time period the more uniformly distributed test points can be chosen meaningful. The first test point should be the first full hour or half hour time point at or after the 10% release point. The last test point should be at the last full hour or half hour time point at or before the 80% release point. The other test point or test points should be in the middle (n=3) or uniformly distributed (n>3) at full hour or half hour time points at or in between the 10 and 80% release phase. The percentage of acceleration or delay is calculated by the arithmetic mean (arithmetic average) of the n values to give the arithmetic mean release.

The term "and/or" in "under in-vitro conditions at pH 1.2 and/or at pH 6.8" means that there may be different meaningful conditions for different pharmaceutical compositions. Resistance against the influence of ethanol shall be determined only in a relevant period of the release of the active ingredient.

For instance immediate release pharmaceutical compositions will release the active ingredient in a short period of time which is usually less than 2 hours. In this case the in-vitro conditions at pH 1.2 which simulate the gastric fluid are sufficient for the test. There is usually no need for testing at pH 6.8.

On the other hand sustained release pharmaceutical compositions have longer periods of the release of the active ingredient for instance from 6 to 12 or even more hours, with usually more than 10% release within the first two hours. In this case it is meaningful to test under in-vitro conditions at pH 1.2 and at pH 6.8.

Enteric coated pharmaceutical compositions are defined to show almost no release or less than 10% release of the active ingredient within the first two hours at pH 1.2. In this case a meaningful testing requires to test the ethanol resistance additionally at the end of the pH 1.2 phase after 2 hours in the medium with and without 40% ethanol. If there is a release of not more than 10% of the total dose at pH 1.2 after 2 hours in the medium with 40% ethanol, the testing can be continued in the 10% to 80% release phase at pH 6.8 as discussed above. If there should be already more than 10% release at pH 1.2 after 2 hours in the medium with 40% ethanol, the enteric pharmaceutical composition is regarded to be not resistant against the influence of ethanol and no more testing at pH 6.8 is required.

Pulsed release pharmaceutical compositions are defined to show a defined lag time of several hours, maybe 4, 5, or 6 hours, with almost no release or less than 10% release of the active ingredient at pH 6.8 before the active ingredient is released in the pulse phase within a comparatively short period of time, maybe 1 or 2 hours. In this case a meaningful testing requires testing the ethanol resistance additionally at the end of the lag phase in the medium with 40% ethanol. If there is a release of not more than 10% of the total dose at the end of the lag phase at pH 6.8 in the medium with 40% ethanol, the testing can be continued in the 10% to 80% release phase at pH 6.8 as discussed above. If there should be more than 10% of the total dose at the end of the lag phase at pH 6.8 in the medium with 40% ethanol, the pulsed pharmaceutical composition is regarded to be not resistant against the influence of ethanol and no more testing at pH 6.8 is required.

The percentages of acceleration or delay under the influence of the 40% ethanol containing medium are calculated by subtraction of corresponding single release values and the calculation of the arithmetic average thereof. The n release values taken from the medium with ethanol are subtracted by the corresponding n release values from the medium without ethanol and the arithmetic average of the differences is calculated. A positive result stands for an acceleration of the release; a negative result stands for a delayed release.

A controlled release pharmaceutical composition which fulfils these conditions can be considered to be resistant against critically accelerated release or delay of the active compound by thoughtlessness or by addictive behaviour of the patients with respect to the use of ethanol or ethanol-containing drinks. This situation relates essentially to the simultaneous or subsequent consumption of an alcoholic drink together with the taking of the controlled release pharmaceutical form, such that the pharmaceutical form is exposed to a strong ethanol-containing medium in the stomach or intestine.

However, the purpose of the present invention is expressively not to stimulate, to promote or to make possible the consumption of ethanol-containing drinks together with delayed-release pharmaceutical forms, but to alleviate or to avoid the possibly fatal consequences of intentional or inadvertent misuse or abuse.

CALCULATION EXAMPLE 1

If the arithmetic average calculated from the active ingredient release in the medium with ethanol and without ethanol is 8% (=plus 8%), then there is an acceleration caused by the influence of ethanol of 8%. In this case the controlled release pharmaceutical composition is regarded to be resistant against the influence of ethanol because it is within the limit of not more than 20% acceleration.

CALCULATION EXAMPLE 2

If the arithmetic average calculated from the active ingredient release in the medium with ethanol and without ethanol is minus 23%, then there is a delay caused by the influence of ethanol of 23%. In this case the controlled release pharmaceutical composition is not regarded to be resistant against the influence of ethanol because it is out of the limit of not more than 20% delay.

Measurement Methods

The measurement of the percentage amount of active ingredient released can be carried out, for example, by on-line UV spectroscopy at a wavelength suitable for the respective active compound. HPLC determination is also possible. The methodology is familiar to a person skilled in the art.

The release of active ingredient can be determined according to USP, in particular USP 32-NF27, General Chapter <711>, *Dissolution*, Apparatus 2 (basket), Method <724> "Delayed Release (Enteric Coated) Articles-General, General Drug Release Standard", Method B (100 rpm, 37° C.), type I basket, with the following modification: The pharmaceutical forms are tested at pH 1.2 for the first 2 hours using 0.1 N HCl medium or at pH 6.8 using a phosphate buffer (European Pharmacopoeia (EP)), which corresponds to an artificial intestinal medium. The measurement in the ethanol containing aqueous medium is carried out using 40% ethanol (v/v) in the medium. If appropriate or required for a certain controlled release pharmaceutical composition, depending on the active ingredient included and the type and size of release form, (small or large pellet or small or large tablet) instead of the basket method the paddle method may be used with 50, 100 or 150 rpm.

Core

The Controlled release pharmaceutical composition according to the present invention comprises a core which comprises a pharmaceutical active ingredient and which may be an uncoated pellet or a coated pellet. The term pellet shall herewith include granules and tablets which can be understood as pellets of larger size.

Uncoated Pellets as Cores

The core may comprise an uncoated neutral carrier pellet, for instance a non-pareilles, on top of which the active ingredient is bound in a binder, such as lactose or polyvinylpyrrolidon. The core may alternatively comprise an uncoated pellet in the form of uncoated polymeric matrix in which the active ingredient is bound. The core may comprise an uncoated pellet consisting of a crystallized active ingredient.

In the case of a core which is an uncoated pellet the coating with the ethanol resistance conferring coating layer has the functions of providing at first the desired release properties function to the pharmaceutical composition and secondly to provide resistance against the influence of ethanol.

Coated Pellets as Cores

The core may comprise a coated pellet which comprises a pharmaceutical active ingredient. The coated pellet may be a readily formulated or a commercially available pharmaceutical composition which shall be coated by the ethanol resistance conferring coating layer in order to confer the release profile of the included pharmaceutical active ingredient to be resistant against the influence of ethanol. The coated pellet may be an immediate release pharmaceutical formulation. The coated pellet may be a sustained release pharmaceutical formulation. The coated pellet may be an enteric coated pharmaceutical formulation.

In the case of a core which is a coated pellet the coating with the ethanol resistance conferring coating layer has the function to compensate the influence of the ethanol so that the original release characteristics remain virtually unchanged within the defined limits of acceptable acceleration or delay.

Coated or Uncoated Tablets as Cores

The core may be a coated or an uncoated tablet, preferably with a size or length in at least one direction of 1 to 50 or 10 to 25 mm. The tablet may for instance have the form of a ball, a sphere, a disk or a torpedo. Preferably an enteric coated (gastric resistant) tablet may be used as a core.

Process of Coating

The invention discloses a process for preparing a controlled release pharmaceutical composition by coating an uncoated or a coated core comprising an active ingredient with the ethanol resistance conferring coating layer by a spray process, preferably by fluidized bed spray coating.

Pelletizing of Cores which are Uncoated Pellets

Cores which are uncoated pellets can be manufactured in a pelletizing process. A rounded, active ingredient-containing pellet with or without a neutral carrier is produced. A rounded, active ingredient-containing substrate with or without a neutral carrier is produced. By means of a fluidized bed process, liquid can be applied to placebo pellets or other suitable carrier materials, the solvent or suspending agent being evaporated. According to the preparation process, a drying step can be added. The spraying step and subsequently drying may be repeated several times until the intended amount of pharmaceutical active ingredient is fully applied. Alternatively wet extrusion, melt extrusion, spray drying, melt granulation or wet granulation may be used to produce uncoated pellets.

The active ingredient is as a rule brought into an organic solvent or into water and mixed. In order to guarantee the satisfactory sprayability of the mixture, it is usually necessary to formulate a mixture with relatively low viscosity. The addition of a detergent, e.g. Tween, in concentrations of 0.1 to 20, preferably 0.5 to 10% by weight, can be advantageous for the reduction of the surface tension.

In addition to the active ingredient, the spray suspension can contain further pharmaceutical excipients: binders, such as lactose, polyvinylpyrrolidone (PVP), moisture retention agents, disintegration promoters, s, disintegrants, starch and its derivatives, sugar solubilizers or others.

Appropriate application processes are known, for example, from Bauer, Lehmann, Osterwald, Rothgang "Überzogene Arzneiformen" [Coated Pharmaceutical Forms] Wissenschaftliche Verlagsgesellschaft mbH Stuttgart, Chap. 7, pp. 165-196.

Details are furthermore known to the person skilled in the art from textbooks. See, for example:
- Voigt, R. (1984): Lehrbuch der pharmazeutischen Technologie [Textbook of Pharmaceutical Technology]; Verlag Chemie Weinheim-Beerfield Beach/Fla.-Basle.
- Sucker, H., Fuchs, P., Speiser, P.: Pharmazeutische Technologie [Pharmaceutical Technology], George Thieme Verlag Stuttgart (1991), in particular chapters 15 and 16, pp. 626-642.
- Gennaro, A., R. (Editor), Remington's Pharmaceutical Sciences, Mack Publishing Co., Easton Pa. (1985), Chapter 88, pp. 1567-1573.
- List, P. H. (1982): Arzneiformenlehre [Pharmaceutical Form Theory], Wissenschaftliche Verlagsgesellschaft mbH, Stuttgart.

Pellet cores can be rounded by processes such as rotor agglomeration, precipitation or spray processes. In particular ultrasonic vortex spray processes can be applied to give still uncoated pellet cores of defined size, e.g. from 100 to 5000 μm. This has the advantage that the entire core volume is available for active ingredient loading. The active ingredient loading can thereby again be increased in relation to the embodiment having an inert core. A process of direct compaction may be used to produce cores for mini tablets. In addition to the pharmaceutical active ingredient, the uncoated pellet core may comprise further pharmaceutical excipients: binders such as lactose, polyvinylpyrrolidone (PVP), humectants, disintegration promoters, s, disintegrants, starch and derivatives thereof, sugar solubilizers or others.

Coated Pellets

The Controlled release pharmaceutical composition according to the invention may be characterized in that the ethanol resistance conferring coating layer is present in an amount of at least 2, at least 3, at least 4, at least 5, preferably 10 to 500% by weight calculated on the weight of core.

The controlled release pharmaceutical composition may preferably be present in the form of coated pellets (cores), minitablets with an overall average diameter from 100-5000 μm, preferably 100 to 2000, most preferably 300 to 1000 μm.

The controlled release pharmaceutical composition according to the invention may be present in the form of coated pellets (cores) with an overall average diameter in the range between 100 to 700 μm, preferably above 200 μm or above 500 μm or in the range between 250 and 400 μm.

The controlled release pharmaceutical composition according to the invention may be present in the form of mini tablets or tablets with an overall average diameter in the range between 1400 to 5000 μm, preferably 1500 to 4000, most preferably 1800 to 3500 μm.

When the coated pellets (cores) have an overall average diameter in the range between 100 to 700 μm, preferably above 200 μm or above 500 μm or in the range between 250 and 400 μm the ethanol resistance conferring coating layer may be present in an amount of at least 20, at least 30, at least 50, at least 100% by weight calculated on the weight of core.

When the coated pellets (cores) have an overall average diameter in the range between 1400 to 5000 μm, preferably above 2000 μm or above 2500 μm or in the range between 2500 and 3500 μm the coating layer should be present in an amount of at least 10, at least 20, at least 30% by weight calculated on the weight of core.

Mini Tablets

By the achievements of the present invention it possible to provide mini tablets, for instance in a size from 1 up to 5 mm, with an ethanol resistance conferring coating layer.

Tablets

By the achievements of the present invention it possible to provide tablets, for instance in a size from 1 up to 50 mm, with a gastric resistant and ethanol resistant coating.

Polymeric Portion a)

The polymeric portion a) is consisting of one or more water insoluble, essentially neutral vinyl polymer or vinyl copolymer. Preferably the polymeric portion a) is present in an amount of at least 3.0, at least 3.2, at least 3.5 at least 9, at least 15, at least 25, at least 35, % by weight calculated on the weight of the core.

Water Insoluble Essentially Neutral Vinyl Polymers or Copolymers

The term a water insoluble, essentially neutral vinyl polymer or copolymer does not necessarily mean one polymer or copolymer a1). The term a water insoluble essentially neutral vinyl polymer or copolymer is meant in the sense of one or more polymers or copolymers a1).

The term water-insoluble essentially neutral vinyl polymers or vinyl copolymers is meant to cover those polymers or copolymers which are water-insoluble over the entire pH range of 1 to 14 and only swellable in water.

A vinyl polymer originates from the polymerization of monomers with vinyl groups such like (meth)acrylic monomers.

The water-insoluble essentially neutral vinyl polymers a1) is present in the polymeric portion a) in amounts of 60 to 99, 75 to 98, 80 to 95 or 85 to 95% by weight, based on the dry weight of the polymeric portion a).

Essentially neutral is meant in the sense in that the polymers, if at all, may contain only small amounts of ionic groups. Even if small amounts of ionic groups are present the physical-chemical behaviour of such polymers is almost the same as the physical-chemical of polymers without any ionic groups. Essentially neutral is especially meant in the sense in that the polymers contain less than 5, less than 4, less than 3, less than 2 or less than 1% by weight of monomer residues with anionic or cationic side groups. Preferably the water-insoluble neutral vinyl polymers or copolymers do not contain any cationic groups. Most preferably the water-insoluble essentially neutral vinyl polymers or copolymers do not contain any ionic groups at all and thus are neutral water-insoluble vinyl polymers (100% neutral).

Water insoluble (meth)acrylic polymers composed of 5 or 10% by weight of monomer residues containing cationic quaternary ammonium groups, e.g. of the type EUDRAGIT® RS or EUDRAGIT® RL, are not suitable for the purposes of the present invention since the resulting pharmaceutical compositions are not sufficiently resistant against the influence of 40% ethanol. Thus water insoluble (meth)acrylic polymers containing at least 1% by weight, at least 2%, at least 3% at least 4% or at least 5% by weight of monomer residues with cationic quaternary ammonium groups may be excluded from the scope of the present invention.

In general, only one or one type of water-insoluble essentially neutral vinyl polymer or copolymer is present in the pharmaceutical composition. However, it is also possible, if appropriate, for two or more water-insoluble polymers or copolymers or types of such polymers or copolymers to be present alongside one another or in a mixture.

Water Insoluble Polymers of the Type of Polyvinyl Acetate

A suitable water insoluble essentially neutral vinyl polymer or copolymer may be of the type of polyvinyl acetate polymers or copolymers derived thereof.

Examples of water insoluble poly vinyl acetate type polymers or copolymers are polyvinyl acetate (PVAc, Kollicoat), vinylacetate-vinylpyrrolidon-copolymer (Kollidon® VA64).

Water Insoluble (Meth)Acrylic Copolymers

A suitable water insoluble, essentially neutral vinyl polymer or copolymer may be most preferred of the type of (meth)acrylic copolymers.

Neutral (Meth)Acrylate Copolymers (EUDRAGIT® NE Type)

Neutral or essentially neutral methacrylate copolymers consist at least to an extent of more than 95% by weight, in particular to an extent of at least 98% by weight, preferably to an extent of at least 99% by weight, more preferably to an extent of 100% by weight, of (meth)acrylate monomers with neutral radicals, especially $C_1$- to $C_4$-alkyl radicals.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% by weight of acrylic acid or methacrylic acid (EUDRAGIT® NE type).

EUDRAGIT® NE and Eudragit® NM are copolymers composed of free-radically polymerized units of 30% by weight of ethyl acrylate and 70% by weight of methyl methacrylate.

A suitable water insoluble polymer is a copolymer composed of free-radical polymerized units of more than 95 up to 100% by weight $C_1$- to $C_4$-alkyl esters of acrylic or of methacrylic acid and less than 5% by weight of acrylic or methacrylic acid.

Excipients Portion b)

The ethanol resistance conferring coating layer further comprises an excipients portion b) consisting of the excipients b1) 100 to 250% by weight of a non-porous inert lubricant, b2) 1 to 35% by weight of a cellulosic compound, b3) 0.1 to 25% by weight of an emulsifier and additionally or alternatively to b3), b4) 0.1 to 30% by weight of a plasticizer whereby the excipients of the excipients portion b) are each calculated on the dry weight of the polymer portion a).

The excipients portion b) may consist of the excipients b1), b2), b3) and b4).

The excipients portion b) may consist of the excipients b1), b2) and b3).

The excipients portion b) may consist of the excipients b1), b2) and b4).

In all cases the excipients cited add to 100%.

The Inert Non-Porous Lubricant b1)

The excipients portion b) of the ethanol resistance conferring coating layer contains 60 to 250, 90 to 240, 110 to 230 or 140 to 220% by weight of a non-porous inert lubricant, calculated on dry weight of the polymeric portion a), Lubricants (sometimes also called glidants) are pharmaceutically acceptable substances which help in preventing agglomeration of polymer coated cores during the coating process.

Porous lubricants like silica powders are not suitable for the purposes of the present invention. Porous structures may possibly cause capillary effects that promote the enhanced penetration of the coating by aqueous alcohol (ethanol) containing media.

Inert means that the lubricant does normally not chemically interact with other substances and is not soluble or only poorly soluble in water and/or ethanol.

Not soluble or only poorly soluble means more than 10 parts by weight of solvent required per 1 part by weight of solute. Furthermore inert non-porous lubricants essentially do not influence the glass transition temperature of the polymer mixture of the coating.

Lubricants like glycerol monostearate (GMS), which can not be applied in sufficient amounts to the coating layer to convey resistance against ethanol containing aqueous media are per se not suitable in the sense of the invention. Thus glycerol monostearate (GMS) is not an inert in the sense of the invention and thus excluded.

The non-porous inert lubricant may be a layered silica component, a pigment or a stearate compound.

The inert lubricant may be Ca- or Mg-stearate. The inert lubricant may be $TiO_2$.

Most preferred is the inert non-porous lubricant talc. Among the different types of talc, talc with a mean particle size, determined by laser diffraction, in the range of 12 to 50, preferred 15-25 µm is preferred over talc with a mean particle size of less than 12 µm, determined by laser diffraction. Talc with a mean particle size, determined by laser diffraction in the range of 12 to 50, preferred 15-25 µm is preferred because it seems to enhance the influence of the total amount of the ethanol resistance conferring coating layer in relation to the core (s. examples 1-6) since both acceleration and delay values are observed (examples 1-3). This opens the opportunity for a fine tuning between acceleration and delay by using the thickness of the coating as a kind of calibration tool. When talc with a mean particle size of less than 12 µm, determined by laser diffraction, is used only acceleration values are observed (examples 4-6), which allows fine tuning on the acceleration side but no fine tuning between acceleration and delay.

Cellulosic Compound b2)

The excipients portion b) of the ethanol resistance conferring coating layer contains 1 to 35, 2 to 30, 5 to 28 or 15 to 25% by weight of a cellulosic compound b2), calculated on dry weight of the polymeric portion a). The cellulosic compound is preferably a neutral cellulosic compound, more preferably a water soluble cellulose derivative. A neutral cellulosic compound may be a neural derivative of cellulose and may be preferably a methyl-, ethyl- or propyl-ether of cellulose. Most preferred the neutral cellulosic compound is hydroxypropylmethylcellulose (HPMC), hydroxyethylcellulose (HEC), sodium-carboxymethylcellulose (Na-CMC) or methylcellulose. The cellulosic compound is thought to protect the ethanol resistance conferring coating layer from being intruded by the ethanol. In the presence of ethanol a kind of swelling might occur which seals pores in the coating layer.

Emulsifier b3)

The excipients portion b) of the ethanol resistance conferring coating layer may contain 0.1 to 25, 0.8 to 20, 1 to 15 or 5 to 12% by weight of an emulsifier, preferably a nonionic emulsifier, calculated on dry weight of the polymeric portion a), The inventors have found that the addition of one or more emulsifiers in the coating seems to improve the resistance of the pharmaceutical composition indirectly. It is supposed that the presence of a detergent in the spraying suspension promotes the film forming process to become more complete. A more complete film seems to be more resistant against the influence of ethanol than a film which was formed without the presence of a certain amount of an emulsifier in the coating. A film which was formed without the presence of certain amounts of an emulsifier in the coating is supposed to be a little more porous than a film which was formed in the presence of the emulsifier. Therefore the action of an emulsifier in the film forming process although not fully understood may be similar but not identical to the effect of curing processes applied to coated pellets. It is further surprising that there seems to be no negative influence or changes of the release profile itself neither when ethanol is present in the medium or not.

Preferably the emulsifier is a polyoxyethylene derivative of a sorbitan ester or a sorbitan ether.

Most preferred the detergent is polyoxyethylene sorbitan monooleate (polyethylene glycol sobitan monooleate, CAS registry number 9005-65-6, for instance Tween® 80).

Plasticizer b4)

The excipients portion b) of the ethanol resistance conferring coating layer may contain 0.1 to 30, 1 to 25, 2 to 22 or 5 to 15% by weight of a (one or more) plasticizer, calculated on dry weight of the polymeric portion a).

Plasticizers may partially or fully substitute the emulsifier component b3). The technical effect might be similar to that contributed by emulsifiers. Plasticizers may influence the functionality of the ethanol resistance conferring coating layer, depending on the type (lipophilic or hydrophilic) and added amount. Plasticizers achieve through physical interaction with the polymers of the polymer mixture a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12 000. Preferred plasticizers are triethyl citrate (TEC), acetyl triethyl citrate (ATEC), diethyl sebacate and dibutyl sebacate (DBS). Mention should additionally be made of esters which are usually liquid at room temperature, such as citrates, phthalates, sebacates or castor oil. Esters of citric acid and sebacinic acid are preferably used.

Addition of the plasticizers to the formulation can be carried out in a known manner, directly, in aqueous solution or after thermal pre-treatment of the mixture. It is also possible to employ mixtures of plasticizers.

Further Pharmaceutical Excipients

If the ethanol resistance conferring coating layer comprises, consists or contains less than 100%, which can be 70, 80, 90, 95 or 99% by weight, of the polymeric portion a) and the excipients portion b), it may further comprise or contain up to 30, up to 20, up to 10, up to 5 or up to 1%, which can be 30, 20, 10, 5 or 1% by weight of further pharmaceutical excipients which are different from the polymers of polymeric portion a) and from the excipients of the excipients portion b). Thus the term further pharmaceutical excipients in the sense of the present invention excludes water insoluble, essentially neutral vinyl polymers or vinyl copolymers, non-porous inert lubricants, cellulosic compounds, emulsifiers or plasticizers. The ethanol resistance conferring coating layer and the further excipients add up 100%. The further excipients do not essentially contribute or influence or interact with the effect of conferring ethanol resistance which is due to the mixture of polymeric portion a) and the excipients portion b). Such further excipients can be for instance pigments. Most preferably no further pharmaceutical excipients are present in the ethanol resistance conferring coating layer.

Further pharmaceutical excipients customary in pharmacy, occasionally also referred to as customary additives, are added to the formulation of the invention, preferably during production of the granules or powders. It is, of course, always necessary for all the excipients or customary additives employed to be toxicologically acceptable and usable in particular in medicaments without a risk for patients.

The amounts employed within the above mentioned frames and the use of the further pharmaceutical excipients in pharmacy for medicament coatings are familiar to the skilled worker. Examples of possible further pharmaceutical excipients customary in pharmacy may be for instance antioxidants, pore formers, gloss agents, aromatizing substances or flavourings. They may serve as processing aids and are intended to ensure a reliable and reproducible production process and good long-term storage stability or they achieve additional advantageous properties in the pharmaceutical form. Further pharmaceutical excipients may be added to the ethanol resistance conferring coating layer preparations before applying the coating by spraying processing.

Multiparticulate Pharmaceutical Forms

The controlled release pharmaceutical composition according to the invention may have the form of pellets, which are contained in a multiparticulate pharmaceutical form, for instance in the form of a compressed tablet, capsules, sachets, effervescent tablets or reconstitutable powders.

Top Coats and Sub Coats

The controlled release pharmaceutical composition according to the invention may be further equipped or coated with a sub coat and/or a top coat.

A sub coat may be located between the core and the coating layer controlling the release of the pharmaceutical active substance (controlling layer). A sub coat may have the function to separate substances of the core from substances of the controlling layer which may be incompatible with each other. The sub coat has essentially no influence on the release characteristics or on the resistance against ethanol. A sub coat is preferably essentially water-soluble, for instance it may consist of substances like hydroxylpropylmethylcellulose (HPMC) as a film former. The average thickness of the sub coat layer is very thin, for example not more than 15 μm, preferably not more than 10 μm.

A top coat may be present and is preferably essentially water soluble. A top coat may have the function of colouring the pharmaceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical excipients like pigments or lubricants in small amounts. The topcoat has essentially no influence on the release characteristics or on the resistance against ethanol.

The expressions sub coat and top coat are well known to the person skilled in the art.

Pigments in a Top Coat

As already stated pigments may be used in the coating layer in the function as non-porous inert lubricants to promote resistance against the influence of ethanol. If pigments are additionally added as excipients which do not contribute to the invention they may be added to a top coat onto the coating layer to give some coloring. The pigments to be used in the function as non-porous inert lubricants in the coating layer or as excipients which do not contribute to the invention are generally of course non-toxic and suitable for pharmaceutical purposes. Concerning this, see also, for example: Deutsche Forschungsgemeinschaft, *Farbstoffe für Lebensmittel*, Harald, Boldt Verlag KG, Boppard (1978); Deutsche Lebensmittelrundschau 74, No. 4, p. 156 (1978); Arzneimittelfarbstoffverordnung AmFarbV of 25 Aug. 1980.

Examples of pigments are titanium dioxide, orange yellow, cochineal red lake, coloured pigments based on alumina or azo dyes, sulphonic acid dyes, orange yellow S (E110, C.I. 15985, FD&C Yellow 6), indigo carmine (E132, C.I. 73015, FD&C Blue 2), tartrazine (E 102, C.I. 19140, FD&C Yellow 5), Ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The E numbers indicated for the pigments relate to an EU numbering. Concerning this, see also "Deutsche Forschungsgemeinschaft, Farbstoffe für Lebensmittel, Harald Boldt Verlag KG, Boppard (1978); Deutsche Lebensmittelrundschau 74, No. 4, p. 156 (1978); Arzneimittelfarbstoffverordnung AmFarbV of 25 Aug. 1980. The FD&C numbers relate to the approval in food, drugs and cosmetics by the U.S. food and drug administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Process for Producing a Pharmaceutical Form According to the Invention

The controlled release pharmaceutical composition according to the invention may be produced in a manner known per se by pharmaceutically customary processes such as direct compression, compression of dry, wet or sintered granules and subsequent rounding off, wet and melt extrusion, wet or dry granulation or direct pelleting or by binding powders (powder layering) onto active ingredient-free beads or neutral cores (nonpareilles) or active ingredient-containing particles and by applying the polymer coating in a spray process or by fluidized bed granulation.

Amounts of the Ethanol Resistance Conferring Coating Layer in Relation to the Core The controlled release pharmaceutical composition according to the invention may be characterized in that the polymeric portion a) is present in an amount of at least 3.0, at least 3.2, at least 3.5% by weight calculated on the weight of the core.

The controlled release pharmaceutical composition according to the invention is characterized in that the core may be a coated or an uncoated pellet which has an average diameter in the range between 100 to 5000 µm. The core may be as well be a coated or an uncoated tablet with a size in at least one direction of 1 to 50 or 10 to 25 mm. The tablet may for instance have the form of a ball, a sphere, a disk or a torpedo.

Small cores have a large surface in comparison to large cores. Thus the amount of ethanol resistance conferring coating layer in % by weight to be sprayed on small cores is in general higher than the amount needed for larger cores to confer the same or similar effect. Since it is difficult to define and to measure the coating thickness in µm, the inventors have classified three types of cores with different average diameters to define suitable ranges of amounts of the ethanol resistance conferring coating layer in % by weight.

A controlled release pharmaceutical composition according to the invention may be characterized in that the core has an average diameter in the range between 100 to 700 µm (small cores) and the amount of polymer dry substance of the polymer portion a) in the ethanol resistance conferring coating layer is from 15 to 200, 25 to 300 or 50 to 500% by weight calculated on weight of the core.

A controlled release pharmaceutical composition according to the invention may be characterized in that the core has an average diameter in the range of above 700 and up to 1400 µm (middle sized cores) and the amount of polymer dry substance of the polymer portion a) in the ethanol resistance conferring coating layer is from 10 to 150, 15 to 200 or 25 to 300% by weight calculated on weight of the core.

A controlled release pharmaceutical composition according to the invention may be characterized in that the core has an average diameter in the range of above 1400 and up to 5000 µm (large cores) and the amount of polymer dry substance of the polymer portion a) in the ethanol resistance conferring coating layer is from 5 to 100, 10 to 120 or 20 to 150% by weight calculated on weight of the core.

Use

The pH-dependent controlled release pharmaceutical composition according to the invention may be used to reduce the risk of enhanced release of the included pharmaceutical active ingredient after oral ingestion by simultaneous or subsequent consumption of ethanol containing drinks (misuse).

EXAMPLES

Model Drug

Studies are conducted using metoprolol succinate and naloxone hydrocloride, as a model drug.

Dissolution Studies

Coated pellets are tested according to USP 32-NF27, General Chapter <711>, *Dissolution*, for the first two hours in simulated gastric fluid pH 1.2 and then in buffered medium at pH 6.8.

Dissolution Parameters:

Naloxone Hydrochloride
  Apparatus: USP Type-I (Basket)
  RPM: 100/min.
  Temperature: 37.5±0.5° C.
  Dissolution volume: 500 ml.
  Withdrawal volume: 5 ml withdrawn manually using pipette, without replenishment of the medium.
  Mode of detection: HPLC Metoprolol Succinate
  Apparatus: USP Type-II (Paddle)
  RPM: 100/min.

Temperature: 37.5±0.5° C.
Dissolution volume: 900 ml.
Mode of detection: online UV-VIS
Dissolution Medium 1:
  Simulated gastric fluid pH 1.2 (European Pharmacopoeia=EP)
Dissolution Medium 2:
  Simulated gastric fluid pH 1.2 (European Pharmacopoeia=EP) with 40% (v/v) ethanol
Dissolution Medium 3:
  Phosphate buffered saline pH 6.8 (European Pharmacopoeia=EP)
Dissolution Medium 4:
  Phosphate buffered saline pH 6.8 (European Pharmacopoeia=EP) with 40% (v/v) ethanol
Polymeric Portion a): Water Insoluble, Essentially Neutral Vinyl Copolymer
  EUDRAGIT® NE is used as water insoluble, essentially neutral vinyl copolymer (polymeric portion a)). EUDRAGIT® NE is composed of free-radically polymerized units of 30% by weight of ethyl acrylate and 70% by weight of methyl methacrylate.
Excipients Portion b)
Non-Porous Inert Lubricant b1):
  Talc Pharma: Talc with a mean particle size determined by laser diffraction 19.3 μm (10 μm determined by sedimentation)
  Talc Pharma M: Talc with a mean particle size determined by laser diffraction 10.5 μm (4.7 μm determined by sedimentation)
Cellulosic Compound b2): Hydroxypropylmethylcellulose
Emulsifier b3): Polysorbat 80
Preparation of Uncoated Cores Comprising the Active Ingredient
  Sugar spheres (non-pareilles) of 1700-2000 microns are loaded with metoprolol succinate or naloxone hydrochlorid in a fluidised bed processor using bottom spray.
Naloxone Hydrochloride
  Polyvinyl pyrrolidone (Kollidon® K25) is used as a binder. 900 g of non-pareilles cores are coated with 270 g metoprolol succinate bound in 80 g binder (Kollidon® K25).
Metoprolol Succinate
  Polyvinyl pyrrolidone (Kollidon® K25) is used as a binder. 900 g of non-pareilles cores are coated with 90 g metoprolol succinate bound in 4.5 g binder (Kollidon® K25). Further 120 g Talc and 30 g silicium dioxide are used as lubricants on the cores.

Drug Layering
  Polyvinyl pyrrolidone (Kollidon® K25) and the active ingredient is dissolved in water while gentle stirring. Lubricants are dispersed in water applying high shear forces. The lubricant suspension is poured into the Polyvinyl pyrrolidone (Kollidon® K25) solution applying gentle stirring. Stirring is continued through the entire coating process.
Coating of the Cores with the Ethanol Resistance Conferring Coating Layer
Coating Suspension Preparation:
  The non-porous inert lubricant, the emulsifier and the cellulosic compound (excipient portion b)) are dissolved or dispersed in water applying high shear forces. The lubricant suspension is poured into the EUDRAGIT® NE dispersion applying gentle stirring. Stirring is continued through the entire coating process.
Coating Process:
  Drug layered pellets are coated with different coating suspensions in a fluidized bed apparatus under appropriate conditions, i.e. a spray rate of approximately 10-20 g/min coating suspension per kg cores and a bed temperature of approximately 25-28° C. Atomizing pressure was 1.5 to 2.2 bar at a nozzle diameter of 1.2 mm. After coating the pellets are fluidised at ca. 40° C. and ca. 45% r.h. for a half hour in a fluid bed processor. The coated pellets are having an average diameter of about 2600-3000 μm.
  The resulting coated cores comprising the active ingredient were tested in the corresponding dissolution media at pH 1.2 and/or pH 6.8 without and with 40% (v/v) ethanol. The results are shown in tables 1-2 and 2-2. Release values in bold figures were used for the calculation of the arithmetic average as discussed before under "Resistance against the influence of ethanol".
Discussion of the Examples
  Examples 1 to 3 compared to examples 4 to 6 show the influence of the type of talc. Comparative example C1 show that no ethanol resistance is achieved with talc alone but without the cellulosic compound (HPMC=hydroxypropylmethylcellulose) and without the emulsifier (Polysorbat 80). Comparative example C2 is without the cellulosic compound (HPMC). Comparative example C3 is without the emulsifier (Polysorbat 80). In both cases no ethanol resistance is observed. Ethanol resistance according to the invention is found in the examples 1 to 9. The examples 2 and 6 show an acceleration of less than 10% in the medium with ethanol.

TABLE 1-2

|  | Example No. | | | | | |
| --- | --- | --- | --- | --- | --- | --- |
|  | 1 | 2 | 3 | 4 | 5 | 6 |
| Drug pellets | Naloxone | Naloxone | Naloxone | Naloxone | Naloxone | Naloxone |
| Polymeric portion a) [wt. %/core] | | | | | | |
| EUDRAGIT NE | 40 | 30 | 20 | 40 | 30 | 20 |
| Excipient portion b) | | | | | | |
| b1) Talc Pharma [wt. %/polymeric portion a)] | 210 | 210 | 210 | | | |
| b1) Talc Pharma M [wt. %/polymeric portion a)] | | | | 210 | 210 | 210 |
| b2) HPMC [wt. %/polymeric portion a)] | 20 | 20 | 20 | 20 | 20 | 20 |
| b3) Polysorbat 80 [wt. %/polymeric portion a)] | 10 | 10 | 10 | 10 | 10 | 10 |
| Total weight gain [wt. %/core] | 136 | 102 | 68 | 136 | 102 | 68 |
| Active release without/with 40% EtOH [v/v] | | | | | | |

TABLE 1-2-continued

| | Example No. | | | | | | | | | | | |
|---|---|---|---|---|---|---|---|---|---|---|---|---|
| | 1 | | 2 | | 3 | | 4 | | 5 | | 6 | |
| 1 h (pH 1.2) | 0.0 | 0.0 | 0.0 | 0.0 | 0.0 | 0.0 | 0.0 | 0.0 | 0.0 | 0.0 | 0.0 | 0.0 |
| 2 h (pH 1.2) | 0.0 | 0.0 | 0.0 | 0.0 | 0.0 | 6.3 | 0.0 | 0.0 | 0.0 | 2.7 | 11.5 | 25.2 |
| 3 h (pH 6.8) | 0.0 | 0.0 | 2.7 | 3.1 | 3.6 | 17.6 | 0.0 | 0.0 | 4.9 | 18.2 | 38.2 | 45.3 |
| 4 h (pH 6.8) | 2.6 | 0.0 | 5.6 | 11.1 | 16.6 | 37.7 | 3.2 | 15.2 | 23.3 | 37.1 | 59.0 | 60.0 |
| 5 h (pH 6.8) | 5.4 | 0.0 | 15.7 | 19.2 | 34.7 | 54.5 | 12.2 | 30.4 | 40.0 | 50.7 | 74.1 | 72.6 |
| 6 h (pH 6.8) | 13.0 | 4.0 | 26.1 | 24.4 | 47.5 | 66.2 | 23.7 | 42.4 | 53.6 | 62.6 | 83.6 | 82.1 |
| 8 h (pH 6.8) | 30.4 | 15.8 | 47.2 | 58.9 | 66.9 | 82.8 | 43.2 | 62.3 | 73.4 | 80.6 | 94.1 | 93.6 |
| 10 h (pH 6.8) | 45.9 | 28.8 | 64.8 | 77.1 | 78.8 | 95.6 | 59.4 | 77.7 | 84.9 | 91.0 | 97.7 | 99.0 |
| 12 h (pH 6.8) | 58.3 | 40.2 | 76.1 | 85.2 | 87.1 | 100.0 | 71.9 | 87.0 | 91.5 | 96.6 | 100.0 | 100.0 |
| 16 h (pH 6.8) | 75.9 | 59.1 | 92.6 | 94.8 | 94.9 | 100.0 | 86.5 | 95.9 | 97.1 | 98.8 | 100.0 | 100.0 |
| 20 h (pH 6.8) | 86.5 | 71.7 | 99.4 | 97.5 | 98.3 | 100.0 | 93.2 | 98.3 | 98.5 | 98.9 | 100.0 | 100.0 |
| 24 h (pH 6.8) | 92.7 | 79.3 | 99.5 | 98.2 | 99.7 | 100.0 | 96.9 | 99.3 | 99.3 | 99.1 | 100.0 | 100.0 |
| Arithmetic average (bold figures) | −15.1 | | +7.0 | | +18.4 | | +17.9 | | +10.2 | | +5.1 | |
| n for calculation | 5 | | 5 | | 5 | | 5 | | 4 | | 4 | |
| Ethanol resistance | yes | | yes | | yes | | yes | | yes | | yes | |

TABLE 2-2

| | Example No. | | | | | |
|---|---|---|---|---|---|---|
| | C1 | 7 | 8 | 9 | C2 | C3 |
| Drug pellets | Metoprolol succinate | Metoprolol succinate | Metoprolol succinate | Naloxone | Metoprolol succinate | Naloxone |
| Polymeric portion a) [wt. %/core] | | | | | | |
| EUDRAGIT NE | 8 | 10 | 20 | 20 | 50 | 12 |
| Excipient portion b) | | | | | | |
| b1) Talc Pharma [wt. %/polymeric portion a)] | 200 | 200 | 200 | | 200 | |
| b1) Talc Pharma M [wt. %/polymeric portion a)] | | | | 200 | | 210 |
| b2) HPMC [wt. %/polymeric portion a)] | | 20 | 20 | 10 | 10 | |
| b3) Polysorbat 80 [wt. %/polymeric portion a)] | | 10 | 10 | 10 | | 10 |
| Total weight gain [wt. %/core] | 24 | 33 | 66 | 64 | 155 | 38.4 |
| Active release without/with 40% EtOH [v/v] | | | | | | |
| 1 h (pH 1.2) | 5.8  78.1 | 10.8  20.2 | 0.0  0.0 | 0.0  0.0 | 0.0  0.0 | 0.0  0.0 |
| 2 h (pH 1.2) | 19.4  97.1 | 63.1  77.9 | 0.0  0.0 | 0.0  13.4 | 2.4  11.5 | 0.0  18.4 |
| 3 h (pH 6.8) | 36.7  100.0 | 79.9  92.0 | 21.8  35.3 | 5.9  33.4 | 7.5  30.5 | 1.8  40.3 |
| 4 h (pH 6.8) | 56.7  100.0 | 91.5  97.5 | 41.4  61.1 | 22.6  47.7 | 15.6  51.2 | 4.7  53.5 |
| 5 h (pH 6.8) | 72.0  100.0 | 95.5  100.0 | 57.3  73.2 | 40.6  60.5 | 26.5  66.2 | 8.5  66.1 |
| 6 h (pH 6.8) | 83.0 | 97.4  100.0 | 68.6  80.3 | 54.4  72.2 | 40.0  76.6 | 12.9  78.4 |
| 8 h (pH 6.8) | 93.7 | | 83.5  87.4 | 75.5  89.9 | 61.8  87.9 | 22.3  88.9 |
| 10 h (pH 6.8) | | | 91.4  93.0 | 86.9  96.2 | 84.2  92.9 | 36.9  94.3 |
| 12 h (pH 6.8) | | | 95.5  96.9 | 93.6  98.0 | 93.8  96.7 | 50.5  94.9 |
| 16 h (pH 6.8) | | | 98.9  99.9 | 98.1  99.9 | | 69.8  94.9 |
| 20 h (pH 6.8) | | | | 99.7  98.9 | | 83.3  94.3 |
| 24 h (pH 6.8) | | | | | | 87.2  93.2 |
| Arithmetic average (bold figures) | +53.1 | +12.3 | +15.2 | +19.3 | +34.5 | +51.8 |
| n for calculation | 4 | 3 | 4 | 4 | 4 | 5 |
| Ethanol resistance | no | yes | yes | yes | no | no |

The invention claimed is:
1. A controlled release pharmaceutical composition, comprising a core comprising a pharmaceutical active ingredient,
wherein:
the core is coated with an ethanol resistance conferring coating layer, which confers ethanol resistance to a release profile of the pharmaceutical active ingredient under in-vitro conditions at pH 1.2 and/or at pH 6.8 in a buffered medium;
wherein ethanol resistance means that the release profile is not accelerated by more than 20% and is not delayed by more than 20% under the influence of a 40% ethanol-containing medium in comparison to a release profile of a medium without ethanol;
the coating layer comprises at least 70% by weight of a mixture of a polymeric portion a) and an excipients portion b);
the polymeric portion a) comprises 60 to 99% by weight of a water insoluble, essentially neutral vinyl polymer or copolymer; and
the excipients portion b) comprises:
b1) 100 to 250% by weight of a non-porous inert lubricant;
b2) 1 to 35% by weight of a cellulosic compound;

b3) 0.1 to 25% by weight of an emulsifier; and additionally or alternatively to b3), b4) 0.1 to 30% by weight of a plasticizer, wherein the percent (%) by weight of each excipient is based on the dry weight of the polymeric portion a).

2. The controlled release pharmaceutical composition of claim 1, wherein the core is a pellet, the core having no coating between it and the ethanol resistance conferring coating.

3. The controlled release pharmaceutical composition of claim 2, wherein the core further comprises a neutral carrier pellet on top of which the pharmaceutical active ingredient is bound in a binder.

4. The controlled release pharmaceutical composition of claim 2, wherein the core further comprises a polymeric matrix in which the pharmaceutical active ingredient is bound.

5. The controlled release pharmaceutical composition of claim 2, wherein the core further comprises a pellet consisting of a crystallized active ingredient.

6. The controlled release pharmaceutical composition of claim 1, wherein the core is a coated pellet, which is coated with the ethanol resistance conferring coating.

7. The controlled release pharmaceutical composition of claim 6, wherein the coated pellet is a sustained release pharmaceutical formulation.

8. The controlled release pharmaceutical composition of claim 6, wherein the coated pellet is an enteric coated pharmaceutical formulation.

9. The controlled release pharmaceutical composition of claim 1, wherein the coating layer comprises up to 20% by weight of at least one further pharmaceutical excipient, which is different from the polymers of the polymeric portion a) and different from the excipients of the excipients portion b).

10. The controlled release pharmaceutical composition of claim 1, wherein the water insoluble, essentially neutral vinyl polymer or copolymer is a copolymer comprising free-radical polymerized units of more than 95% and up to 100% by weight of $C_1$- to $C_4$-alkyl esters of acrylic or of methacrylic acid and less than 5% by weight of acrylic or methacrylic acid.

11. The controlled release pharmaceutical composition of claim 1, wherein the water insoluble, essentially neutral polymer or copolymer is a polyvinyl acetate type polymer or a polyvinyl acetate type copolymer.

12. The controlled release pharmaceutical composition of claim 1, wherein the non-porous inert lubricant is a layered silica component, a pigment or a stearate compound.

13. The controlled release pharmaceutical composition of claim 12, wherein the non-porous inert lubricant is talc.

14. The controlled release pharmaceutical composition of claim 12, wherein the non-porous inert lubricant is Ca- or Mg-stearate.

15. The controlled release pharmaceutical composition of claim 1, wherein the cellulosic compound is a water soluble cellulose derivative.

16. The controlled release pharmaceutical composition of claim 15, wherein the cellulosic compound is hydroxypropylmethylcellulose, hydroxyethylcellulose, sodium-carboxymethylcellulose or methyl cellulose.

17. The controlled release pharmaceutical composition of claim 1, wherein the emulsifier is present and is a non-ionic emulsifier.

18. The controlled release pharmaceutical composition of claim 17, wherein the emulsifier is polyoxyethylene derivative of a sorbitan ester or a sorbitan ether.

19. The controlled release pharmaceutical composition of claim 17, wherein the emulsifier is a polyethoxy sorbitan monooleate.

20. The controlled release pharmaceutical composition of claim 1, wherein the pharmaceutical active ingredient has a solubility in ethanol which is classified as slightly soluble according to the USP Pharmacopeia references tables.

21. The controlled release pharmaceutical composition of claim 1, wherein the pharmaceutical active ingredient is an opioid or an opioid antagonist.

22. The controlled release pharmaceutical composition of claim 21, wherein the pharmaceutical active ingredient is morphine or naloxone or a pharmaceutically acceptable salt thereof.

23. The controlled release pharmaceutical composition of claim 1, wherein the pharmaceutical active ingredient has solubility in ethanol which is classified as sparingly soluble according to the USP Pharmacopeia references tables.

24. The controlled release pharmaceutical composition of claim 23, wherein the pharmaceutical active ingredient is metoprolol or a pharmaceutically acceptable salt thereof.

25. The controlled release pharmaceutical composition of claim 1, wherein the controlled release pharmaceutical composition is in at least one form selected from the group consisting of a pellet contained in a multiparticulate pharmaceutical form, a compressed tablet, a capsule, a sachet, an effervescent tablet, a reconstitutable powder.

26. The controlled release pharmaceutical composition of claim 1, further comprising a top coat.

27. The controlled release pharmaceutical composition of claim 1, wherein the coating layer comprises at least 3.0% by weight of the polymeric portion a) based on the weight of the core.

28. The controlled release pharmaceutical composition of claim 1, wherein the core has an average diameter of 100 to 5000 μm.

29. The controlled release pharmaceutical composition of claim 28, wherein:

the core has an average diameter in the range of 100 to 700 μm; and the amount of a polymer dry substance of the polymer portion a) is from 15 to 200% by weight based on the weight of the core.

30. The controlled release pharmaceutical composition of claim 28, wherein:

the core has an average diameter in the range of above 700 and up to 1400 μm; and the amount of a polymer dry substance of the polymer portion a) is from 10 to 150% by weight based on the weight of the core.

31. The controlled release pharmaceutical composition of claim 28, wherein:

the core has an average diameter in the range of above 1400 and up to 5000 μm; and the amount of a polymer dry substance of the polymer portion a) is from 5 to 100% by weight based on the weight of the core.

32. The controlled release pharmaceutical composition of claim 1, wherein the core is an uncoated or a coated tablet.

33. A process for preparing the controlled release pharmaceutical composition of claim 1, comprising coating an uncoated or a coated core comprising the pharmaceutical active ingredient with the coating layer by a spray process or by fluidized bed spray coating.

34. A method of conferring ethanol resistance to a pharmaceutical composition, comprising coating a core comprising a pharmaceutical active ingredient with the coating layer of claim 1, wherein the ethanol resistance reduces the risk of enhanced or reduced release of the pharmaceutical active ingredient after oral ingestion by simultaneous or subsequent consumption of ethanol.

35. The controlled release pharmaceutical composition of claim 1, wherein component b3) is present.

36. The controlled release pharmaceutical composition of claim 35, wherein component b1) comprises talc, component b2) comprises a hydroxypropylmethylcellulose, and component b3) comprises a polyethylene glycol sorbitan monooleate.

* * * * *